United States Patent
Laakso et al.

(10) Patent No.: US 6,861,064 B1
(45) Date of Patent: Mar. 1, 2005

(54) ENCAPSULATION METHOD

(75) Inventors: Timo Laakso, Höllviken (SE); Mats Reslow, Lund (SE)

(73) Assignee: Jagotec AG, Müttenz (CH)

( * ) Notice: Subject to any disclaimer, the term of this patent is extended or adjusted under 35 U.S.C. 154(b) by 0 days.

(21) Appl. No.: 09/529,442
(22) PCT Filed: Sep. 24, 1998
(86) PCT No.: PCT/SE98/01717

§ 371 (c)(1),
(2), (4) Date: Apr. 13, 2000

(87) PCT Pub. No.: WO99/20253

PCT Pub. Date: Apr. 29, 1999

(30) Foreign Application Priority Data

Oct. 23, 1997 (SE) ............................................... 9703874

(51) Int. Cl.$^7$ ............................................. A01N 25/28
(52) U.S. Cl. ..................... 424/408; 264/4.7; 424/420; 424/498; 427/213.3; 427/213.34
(58) Field of Search .......................... 264/4.6, 4.3, 4.5, 264/4.7; 424/419, 498, 408, 420; 427/213.3, 213.34

(56) References Cited

U.S. PATENT DOCUMENTS

| | | |
|---|---|---|
| 4,166,800 A | 9/1979 | Fong |
| 4,384,975 A | 5/1983 | Fong |
| 4,568,559 A | 2/1986 | Nuwayser et al. |
| 4,652,441 A * | 3/1987 | Okada et al. .................. 424/19 |
| 4,673,595 A | 6/1987 | Orsolini et al. |
| 4,675,189 A | 6/1987 | Kent et al. |
| 4,822,535 A * | 4/1989 | Ekman et al. ............... 264/4.3 |
| 5,000,886 A | 3/1991 | Lawter et al. |
| 5,019,400 A | 5/1991 | Gombotz et al. |
| 5,407,609 A * | 4/1995 | Tice et al. ..................... 264/46 |
| 5,578,709 A | 11/1996 | Woiszwillo |
| 5,589,167 A | 12/1996 | Cleland et al. |
| 5,654,010 A | 8/1997 | Johnson et al. |

FOREIGN PATENT DOCUMENTS

| | | |
|---|---|---|
| EP | 052510 | 5/1982 |
| EP | 0 052 510 A2 | 5/1982 |
| SE | 462780 | 10/1985 |
| WO | WO 90/13780 | 11/1990 |
| WO | WO 96/07399 | 3/1996 |
| WO | WO 96/40074 | 12/1996 |

OTHER PUBLICATIONS

"Biodegradable poly(lactic acid) and poly(lactide–co–glycolide) microcapsules: problems associated with preparative techniques and release properties", R. Jalil and J.R. Nixon, *J. Microencapsulation*, vol. 7, No. 3, pp. 297–325 (1990).
1976 Registry of Toxic Effects of Chemical Substances.
"Carcinogenic Studies on Water–Soluble and Insoluble Macromolecules", W.C. Hueper, *Archives of Pathology*, vol. 67, pp. 589 to 617 (1959).
"Development of Stable Protein Formulations for Microencapsulation in Biodegradable Polymers" Jeffrey L. Cleland and Andrew J.S. Jones, *Proceedings of International Symposium on Controlled Release of Bioactive Materials*, vol. 22, pp. 514 to 515 (1995).

* cited by examiner

*Primary Examiner*—Neil S. Levy
(74) *Attorney, Agent, or Firm*—Mintz Levin Cohn Ferris Glovsky and Popeo PC; Daniel F. Coughlin

(57) ABSTRACT

A novel method of encapsulating an active substance in a biodegradable polymer, which comprises: a) dissolving said biodegradable polymer in an organic solvent therefor; $b_1$) dispersing said active substance in the organic solution obtained in step a) to provide a dispersion with the active substance as the inner phase thereof; or alternatively $b_2$) emulsifying said active substance, dissolved in water or other aqueous solvent therefor, in the organic solution obtained in step a) to provide an emulsion with the active substance as the inner aqueous phase thereof; and c) subjecting the dispersion obtained in step $b_1$), or alternatively the emulsion obtained in step $b_2$), to an encapsulation operation with an aqueous polyethylene glycol solution as a continuous phase to provide micro- or nanoparticles having the active substance encapsulated therein. Sustained release particles obtainable thereby.

6 Claims, 1 Drawing Sheet

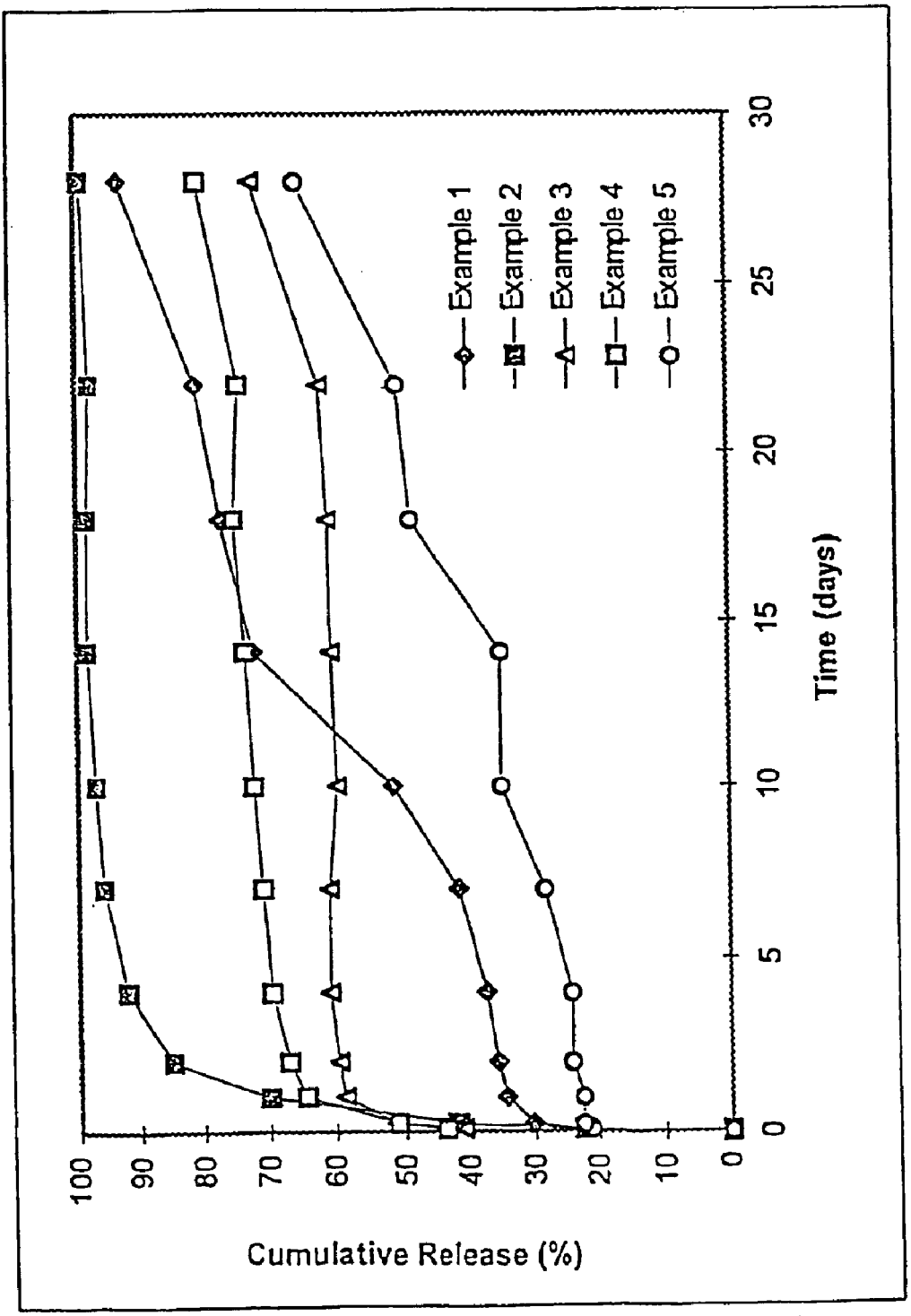
FIGURE

ENCAPSULATION METHOD

This application is the national phase under 35 U.S.C. § 371 of PCT International Application No. PCT/SE98/01717, which has an international filing date of Sep. 24, 1998, which designated the United States of America and which claims priority on Swedish Patent Application number 9703874-9, filed on Oct. 23, 1997, the entire contents of which are hereby incorporated herein by reference.

FIELD OF INVENTION

The present invention is within the field of encapsulating active substances, e.g. drugs, in biodegradable polymers. More specifically the invention relates to a novel advantageous encapsulation method which is suitable for water soluble as well as water insoluble active substances and which gives highly active micro as well as nanoparticles with high encapsulation efficiency.

BACKGROUND OF THE INVENTION

The encapsulation of materials may provide beneficial properties. For example, drugs that are encapsulated may provide increased stability, longer duration of action and increased efficiency. For convenience drugs are often encapsulated in solid materials which have a size suitable for injection, that is generally below 200 µm in diameter, and then the process is referred to as a microencapsulation.

Microencapsulation processes may yield microcapsules, microspheres or microparticles. Microcapsules consist of a core and a shell that covers the core. The core may be composed of another polymer than the shell or of another material altogether, e.g. of the active substance itself. The active substance is generally located in the core but may also be located in the outer shell. Microspheres are spherical in shape and have a more homogenous matrix. Microparticle is a more general term than microspheres in that it is not restricted to spherical shapes. Sometimes it can be difficult to distinguish between microcapsules, microspheres and microparticles, and the term microparticles will be used herein with reference to all three classes.

Methods of preparing microparticles in the prior art have been described extensively in both the patent and the scientific literature (see e.g. Jalil R, Nixon J R. Biodegradable poly(lactic acid) and poly(lactide-co-glycolide) microcapsules: problems associated with preparative techniques and release properties. *J Microencapsul* 1990;7:297–325). They may generally be classified in three types, which are exemplified below in connection with the preparation of microspheres of poly(lactide-coglycolide) (PLGA). PLGA is a well accepted polymer for preparing sustained release microspheres and often the first choice for preparing biocompatible microspheres intended for parenteral administration in humans. Said polymer is not soluble in water.

1. Phase separation techniques using coacervating agents, or non solvents, such as mineral oils and vegetable oils. The active substance, e.g. a polypeptide is first dissolved in the aqueous phase of a water-in-oil emulsion. The polypeptide can also be dispersed directly in the polymer phase as a fine powder. Polymer is precipitated either around the aqueous droplets, or on the polypeptide powder, by the addition of a non-solvent for the polymer, such as silicon oil. Then a hardening agent is added to extract the organic solvent from the micro-spheres. The main disadvantage with said process is the large amount of organic solvent needed for extraction and for washing. The previously used hardening agents including freons, hexane, heptane, cyclohexane and other alkane solvents leave substantial amounts of hardening agents residues in the microspheres and/or necessitate extensive procedures for removing the solvent. Often very large amounts of the second organic solvent are needed and they are often undesirable for health, economical and environmental reasons. Examples in the prior art include heptan (EP 0 052 510), aliphatic fluorinated and fluorohalogenated hydrocarbons sold as FREONS (SE 462 780), and other (U.S. Pat. No. 5,000,886). A further drawback when using e.g. an alkane hardening solvent is that it is flammable. Another drawback is the impact thereof on the environment.

2. Spray drying and spray coating

In spray drying the polymer and the drug are mixed together in a solvent for the polymer. The solvent is then evaporated by spraying the solution. This results in polymeric droplets containing the drug. However, sensitive substances such as proteins can be inactivated during the process due to the elevated temperatures used and the exposure to organic solvent/air interfaces. Further disadvantages include generation of high porosity due to rapid removal of the organic solvent. A variation that has been introduced to avoid these shortcomings is the use of low temperature during microsphere formation (U.S. Pat. No. 5,019,400, WO 90/13780 and U.S. Pat. No. 4,166,800). Microcapsules have been prepared using spray coating of drug-containing microparticles with PLGA polymers (U.S. Pat. No. 4,568,559).

3. Solvent evaporation

In solvent evaporation techniques the polymer is dissolved in an organic solvent which contain the dispersed active drug, the solution then being added to an agitated aqueous outer phase which is immiscible with the polymer. The aqueous outer phase usually contains surfactants to stabilise the oil-in-water emulsion and to prevent agglomeration. The emulsifier used is typically polyvinylalcohol. Emulsifiers are included in the aqueous phase to stabilise the oil-in-water emulsion. The organic solvent is then evaporated over a period of several hours or more, thereby solidifying the polymer to form a polymeric matrix. The solvent can also be extracted by adding the above mentioned suspension to a large volume of water (U.S. Pat. No. 5,407,609).

The final formulation to be used for pharmaceutical applications, especially for parenteral administration, should consist of discrete, non-agglomerated microspheres with the desired size distribution and containing no toxic or in any other way undesirable substances. In order to obtain preparations having the characteristics described above it is necessary to use emulsifiers. The emulsifier can serve several purposes: (1) assist in obtaining the correct droplet size distribution of the emulsion; (2) stabilise the oil-in-water emulsion to avoid coalescence of the droplets; and (3) prevent the solidified microspheres from sticking to each other. The most commonly used emulsifier for preparing PLGA microspheres is polyvinyl alcohol. However, since polyvinyl alcohol is listed in the 1976 Register of Toxic Effects of Chemical Substances and is also implicated as carcinogenic when introduced parenterally into animals ("Carcinogenic studies on Water-Soluble and Insoluble Macromolecules", Archives of Pathology, 67, 589–617, 1959) it is considered undesirable for pharmaceutical preparations administered by injection. This problem has been recognized and attempts of replacing polyvinyl alcohol with other emulsifers can be found in the prior art, for example in U.S. Pat. No. 4,384,975, wherein a carboxylic acid salt surfactant, e.g. sodium oleate was used to stabilise an oil-in-water emulsion. However, despite its drawbacks polyvinyl alcohol is still the most videly used surfactant. However, for the above-mentioned reasons it would be highly desirable to avoid the use of polyvinyl alcohol and other surfactants in microsphere preparations.

Solvent evaporation works well for hydrophobic drugs but for hydrophilic drugs, such as many peptides and proteins, the amount of incorporated drug can be low due to loss of drug to the aqueous phase which is used to extract the organic solvent. Attempts to circumvent this problem include modifying the hydrophilic drug into a less soluble form (WO 96/07399) increasing the viscosity of the inner aqueous solution containing the active drug in a process where a water-in-oil emulsion is first created and the organic solvent then extracted with water (U.S. Pat. No. 4,652,441) and reducing the time available for diffusion (U.S. Pat. No. 5,407,609).

Further, the use of the commonly employed organic solvents, like methylene chloride or ethyl acetate, often results in loss of biological activity for sensitive drugs. Thus, for instance for proteins the three dimensional conformation which is required for biological activity is often lost. Attempts to circumvent this problem includes modification of the active substance into a more stable form (U.S. Pat. No. 5,654,010 and WO 96/40074) keeping the temperature as low as possible during the process (WO 90/13780), and using different protein stabilisers (U.S. Pat. No. 5,589,167, Cleland J L, Jones AJS, "Development of stable protein formulations for microencapsulation in biodegradable polymers". Proceedings of the International Symposium on Controlled Release of Bioactive Materials 1995;22:514–5). However, proteins are generally sensitive to organic solvents and reducing or eliminating the exposure is highly desirable.

Another disadvantage with the solvent evaporation method is the need for using high shear mixing in order to obtain small microspheres- or nanospheres. This may result in degradation or conformational changes of the active substance, especially if it is a protein which is dependent on a three dimensional conformation for its biological activity. The use of high shear mixing is also energy consuming.

In connection with the prior art it can also be added that processes for preparing microspheres from polymers soluble in water are known from e.g. U.S. Pat. No. 4,822,535 and U.S. Pat. No. 5,578,709. In said processes two mutually immiscible aqueous liquid phases are used, of which one is solidified into microspheres. However, as said, these methods cannot be used for the preparation of microspheres from polymers that cannot be dissolved in water.

The present invention relates to a novel method of encapsulating active substances in biodegradable polymers by which the prior art disadvantages are eliminated or at least essentially reduced. For instance the invention makes it possible to obtain high incorporation efficiency of the active substance in the biodegradable polymer and/or to accomplish smaller microparticles or even nano-particles containing highly active doses of the active substances. Furthermore, the amounts of organic solvents are highly reduced. As compared to previously used methods the invention also enables a reduction of the energy input required to obtain micro- or nanoparticles.

OBJECTS OF THE INVENTION

One object of the invention is to provide a method of preparing controlled or sustained release particles having a high entrapment of water soluble substances, e.g. sensitive drugs, without the use of large volumes of organic solvents.

Another object is to provide a method wherein-low energy mixing is utilized only, which is also advantageous in connection with sensitive substances.

Still another object is to provide a method by which small particle sizes, such as micro or even nano size particles, can be obtained in a simple way.

One other object is to provide a method by which the requirement for using PVA and other surfactants is eliminated.

Other objects of the invention should be clear to a person skilled in the art when reading the description above and below.

SUMMARY OF THE INVENTION

More specifically the present invention relates to a method of encapsulating an active substance in a biodegradable polymer, which method comprises:

a) dissolving said biodegradable polymer in an organic solvent therefor;

$b_1$) dispersing said active substance in the organic solution obtained in step a), to provide a dispersion with the active substance as the inner phase thereof; or alternatively $b_2$) emulsifying said active substance, dissolved in water or other aqueous solvent therefor, in the organic solution obtained in step a), to provide an emulsion with the active substance as the inner aqueous phase thereof; and c) subjecting the dispersion obtained in step $b_1$), or alternatively the emulsion obtained in step $b_2$), to an encapsulation operation with an aqueous polyethylene glycol solution as a continuous phase, so as to obtain micro- or nanoparticles having the active substance encapsulated therein.

Thus, according to one aspect of the invention there is provided a simple method of preparing micro- or nanoparticles containing a sensitive biologically active material, e.g. a protein, while using minimal amounts of organic solvent. It has surprisingly been found possible to replace the normally used organic solvent as the continous or extraction phase by an aqueous solution of the non-toxic and pharmaceutically acceptable polymer polyethylene glycol (polyethylene oxide) as a continuous phase and as an extraction medium.

It has also been found that the uptake of active ingredient into the particles can be markedly improved by said use of polyethylene glycol in water or other aqueous solvent as outer(external) phase. The use of solvent evaporation techniques with an aqueous outer phase often results in poor encapsulation as water soluble polypeptides are distributed also to the external phase, especially when small microspheres are obtained. With the present invention high loading combined with small particle size can be obtained provided that the concentration of polyethylene glycol, and other conditions, are controlled such that the active substance is not distributed to the outer phase.

The microparticles can easily be washed and rinsed with water, which is an advantage as compared to the phase separation technique where large amounts of organic solvents are used. Other surprising findings in connection with the use of polyethylene glycol/aqueous solvent as outer phase is that small sized particles are obtained even with low mixing forces and that no surfactants are needed.

The obtained microparticles are well suited for sustained release purposes and are especially adapted for oral or parenteral administration. When prepared with sizes or diameters of less than 10 $\mu$m, and preferably 0.5–3 $\mu$m, they are also suitable for nasal or pulmonal administration to provide either local or systemic effect.

In addition to the unexpected findings referred to above it should also be noted that polyethylene glycol (PEG) is previously known per se to have unique properties for a variety of biotechnical and biomedical applications, which makes the present invention even more advantageous for biotechnical and biomedical applications.

These unique properties are e.g. summarized in Harris, J. M. (ed) Poly(ethylene glycol) chemistry: biotechnical and biomedical applications. 1992, Plenum Press, New York.

PEG has unique properties of major importance for its use in a variety of biotechnical and biomedical applications. One of these is its outstanding effectiveness in excluding other polymers from the volume it occupies in a water solution, which has been utilised to obtain rejection of proteins e.g. in liposomes and small particles with long circulation times after intravenous injection, hospitability to biological materials, non-immunogenicity and non-antigenicity. Another is the formation of aqueous two-phase systems with other polymers (Per Ake Albertsson, Partition of cell particles and macromolecules. Separation and purification of biomolecules, cell organelles, membranes, and cells in aqueous polymer two-phase systems and their use in biochemical analysis and biotechnology. Third Edition, 1986, John Siley & Sons). PEG is non-toxic and generally harmless to proteins and cells. Of the numerous applications of PEG can be mentioned: (1) as a co-solvent for some drugs for injection, (2) as a volume-excluder to increase the concentration of e.g. proteins to induce crystallization, (3) as a part of aqueous two-phase systems used for e.g. purification of biological materials under mild conditions, (4) induction of cell fusion to obtain e.g. hybridomas used for production of monoclonal antibodies, (5) covering the surface of e.g. liposomes and nanoparticles to increase their residence time in the circulation, and (6) covalent attachment of PEG to proteins to obtain conjugates which are still biologically active but no longer immunogenic and antigenic; such PEG-protein adducts having been approved for parenteral use in humans.

PEGs are also sometimes referred to as poly(ethylene oxide) PEO, poly(oxyethylene) and polyoxirane. In general usage, poly(ethylene glycol) refers to molecular weights below 20000, and poly(ethylene)oxide refers to higher molecular weights polymers. In other words the term polyethylene glycol as used in connection with the invention covers also poly(oxyethylene) and polyoxirane.

These objects as well as other objects and advantages of the present invention will become apparent to those skilled in the art from the description following below.

DETAILED DESCRIPTION OF THE INVENTION

The active substances to be used in the method of the invention are preferable biologically active subtances, e.g. drugs, such as proteins, peptides, polypeptides, polynucleotides, oligonucloetides, plasmides or DNA. Examples of protein drugs are growth hormone, erythropoietin, interferon($\alpha,\beta,\gamma$-type), vaccines, epidermal growth hormone and Factor VIII. Examples of peptide drugs are LHRH analogues, insulin, somatostatin, calcitonin, vasopressin and its derivatives.

In the case of proteins they can also be complexed with various substances, e.g. metals, amino acids, salts, acids, bases and amines, to decrease solubility or increase stability. They can further be prepared in the form of a pro-drug or PEG can be attached e.g. to the proteins to increase solubility or stability, modify pharmacokinetics or reduce immunogenicity.

Examples of non-protein drugs suitable for use in the method of the invention can be found for example in the following groups:
anti-tumor agents, antibiotics, anti-flammatory agents, antihistamines, sedatives, muscle relaxants, antiepileptic agents, antidepressants, antiallergic agents, bronchodilators, cardiotonics, antiarrythmic agents, vasodilators, antidiabetic agents, anticoagulants, hemostatics, narcotic agents and steroids.

The active substances which can be encapsulated in accordance with the method claimed are, however, not restricted to biologically active substances, non-biological substances can be encapsulated, e.g. pesticides, fragrances, flavouring agents, catalysts and herbicides.

The proper amount of active substance to be encapsulated is dependent on type of substance, duration time and desired effect, and is of course controlled to an amount that is in each specific case encapsulable by the method according to the invention. Generally said amount is chosen within the range of about 0,001% to 90%, preferably about 0,01 to 70%, more preferably about 0.1 to 45%, and most preferably about 0.1 to 40%, said percentages being by weight based on the weight of the final particles.

In the case of a drug the substance can be used per se or in the form of a pharmaceutical salt. When the drug has a basic group, such as amino groups, it can form salts with carbonic acid, hydrochloric acid, sulphuric acid, acetic acid, citric acid, methanesulfonic acid or the like. When the drug has an acidic group, such as a carboxyl group, it can form salts with metals(e.g. $Ca^{2+}$, $Zn^{2+}$), organic amines (e.g. ethanolamine) or basic amino acids (e.g. arginine). The drug can further be precipitated using various means, optionally followed by size reduction, such as precipitation with divalent metals (e.g $Ca^{2+}$, $Zn^{2+}$). The drug may also be crystallized.

The biodegradable polymer that can be used in the present invention is not limited to any specific material as long as it can be dissolved in an organic solvent and is slightly soluble or insoluble in the outer phase, e.g. poly(ethylene glycol)/aqueous phase and is otherwise, suitable for the preparation of sustained release micro- or nanoparticles.

Preferably the biodegradable polymer used in the method claimed has a weight average molecular weight in the range of about 2000 to 200000, more preferably about 2000 to 110000.

Examples of biodegradable polymers are polyesters, poly-$\beta$-hydroxybutyric acid, polyhydroxyvaleric acid, polycaprolactone, polyesteramides, polycyanoacrylates, poly(amino acids), polycarbonates and polyanhydrides.

A preferred biodegradable polymer is an aliphatic polyester, e.g. homo or copolymers prepared from $\alpha$-hydroxy acids, preferably lactic acid and glycolic acid, and/or cyclic dimers of $\alpha$-hydroxy acids, preferably lactides and glycolides.

When lactic acid/glycolic acid are used as the above-mentioned polymers, the composition or weight ratio (poly) lactic acid/(poly)glycolic acid is preferably about 99/1 to 35/65, more preferably 95/5 to 50/50. They may be used in the form of a copolymer or a mixture of these two or more polymers. The exact composition of the polymer depends on the desired release kinetics, especially the duration of release.

The organic solvent used in step A can be any solvent that is capable of forming an emulsion with a water/PEG mixture, can be removed from the oil droplets through said water/PEG mixture and is capable of dissolving the biodegradable polymer. In other words the solvent should be immiscible, or essentially immiscible, but slightly, or very slightly, soluble in said water/PEG mixture. Examples of suitable solvents are ethyl acetate, dichloromethane, methyl ethyl ketone and methyl isobutyl ketone. These solvents can be used alone or in combinations.

The inner aqueous phase may contain agents for controlling the stability and, if desired, the solubility of the biologically active substance. Such agents may be pH controlling agents and stabilizers for drugs or other active substances.

As can be gathered from the above-mentioned the method according to the invention can be utilized to encapsulate water soluble as well as water insoluble active substances.

Examples of embodiments of these two cases will now be presented below.

The encapsulation method, as exemplified by a water soluble drug, such as a peptide or protein drug can comprise the following steps. The drug solution is prepared in any conventional way and optionally while using pH controlling or drug stabilizing agents. This aqueous solution of the drug, which is to form the inner aqueous phase, is poured into an external (oil) phase containing a biodegradable polymer dissolved in a suitable organic solvent and the mixture is emulsified to provide a W/O emulsion. The emulsification can be prepared using conventional emulsification techniques, such as, propeller mixing, turbine mixing, ultra-sonication or use of static mixers.

If the active substance is to be dispersed directly in the polymer solution, without being dissolved in water, the drug should have a suitable particle size. A suitable particle size is about 0.5–20 $\mu$m, preferably 0.5-10 $\mu$m, such as 0.5-3 $\mu$m. Otherwise, the dispersion step can be carried out as described above for the emulsification step.

The resulting W/O emulsion/dispersion is then subjected to an encapsulation operation. The W/O emulsion/dispersion is added to an aqueous solution containing polyethylene glycol. The polyetylene glycol/aqueous solution is stirred during the addition of the active substance/polymer solution. The W/O emulsion/dispersion can also be mixed with the polyethylene glycol solution by using motionless mixers.

Typically the molecular weight of the polyethylene glycol is within the range of about 1000 to 40000 Da, preferably 5000 to 35000 Da. Depending on said molecular weight, and the properties of the substance to be encapsulated, the concentration of polyetylene glycol is controlled within the range of 20–80% (w/w), preferably 20–60% (w/w), such as 30–55% (w/w) or 30–50% (w/w). In other words a relatively high PEG concentration is used in the outer phase, to obtain a stable emulsion and to prevent diffusion of active ingredient from the droplets/particles. The determination of the optimal concentration can be made by experimentation that is relatively straightforward to someone skilled in the art.

The particles thus formed are generally collected by centrifugation or filtration and rinsed with distilled water or suitable aqueous buffers, several times to remove the excess of polyethylene glycol from the surfaces. To prevent aggregation during the washing and drying procedure, mannitol, Tween 80, or other suitable substances, may be added to the rinsing water. The particles thus obtained can then be dried by conventional means, for instance in vacuum or by a streaming nitrogen gas flow or by lyophilization or air suspension drying.

The particle sizes of the particles obtained by the invention are dependent on the desired uses of said particles as is well known within this technical field. Thus, for instance, when the particles are intended for injection, the particle size should satisfy the dispersibility and needle passage requirements. Furthermore, the particles can be handled or treated in any manner previously known to a person skilled in the art. Thus, a controlled release injectable preparation of said particles can e.g. be dispersed with a suspending agent, containing e.g. mannitol, polysorbate 80, or sodium carboxymethylcellulose.

Other embodiments of the method according to the invention are defined in sub-claims or in the Examples presented below.

According to a second aspect of the invention there are also provided sustained release micro or nanoparticles per se containing an active substance encapsulated in a biodegradable material, which particles are obtainable by a method as claimed in any one of the method claims.

Thus, preferable embodiments thereof are the same as those embodiments which are described in connection with the method. Especially preferable are, however, particles which are adapted for oral, parenteral, nasal or pulmonal administration of the active substance.

Furthermore, for the manufacture of pharmaceutical preparations for oral administration, the microspheres prepared by the method described may be formulated with an excipient (e.g. lactose, sucrose, starch etc.), a disintegrant (e.g. starch, calcium carbonate, etc.), a binder (e.g. starch, gum arabic, carboxymethylcellulose, polyvinylpyrrolidone, etc.) and/or a lubricant(e.g. talc, magnesium stearate, polyethylene glycol etc.) and the resulting composition can be compression-molded in conventional manner. The particles can also be filled into gelatine capsules.

In the accompanying drawing figure the results of in vitro release tests are presented for particles obtained by the method of the present invention as well as particles obtained in line with the prior art.

The manufactures of said particles and the test method are described in Examples 1–5 and the results are presented as cumulative release in % versus time in days.

In this context it can also be added that the release profile can be controlled by factors well known to anyone skilled in the art, e.g. the composition of the polymer used for encapsulating the active material, the solubility of the material, addition of substances affecting the solubility of the active material and/or degradation of the polymer, the amount of active material in the microparticles and the size of the microparticles;

EXAMPLE 1

The following procedure was used to encapsulate bovine serum albumin (BSA) in PLGA (poly(DL-lactide-coglycolide)). First a polymer solution was prepared by dissolving 0.47 g of PLGA (RG504H, Boehringer Ingelheim) in 3 ml of ethyl acetate in a test tube. Then, 44 mg of BSA, (bovine serum albumin; Sigma A-0281) was dissolved in 300 $\mu$l of 10 mM Na-phosphate buffer pH 6.4. The BSA solution was added to the polymer solution and the BSA was homogenously dispersed in the polymer solution by vortex mixing (VF2, IKA-WERK) for one minute. The dispersion was placed in a 5 ml syringe with an 18 G needle.

A 500 ml beaker containing 300 ml of. 40%(w/w) polyetylene glycol 20000 was fitted with a 4-bladed propeller stirrer. The BSA/polymer dispersion was transferred to the beaker by slowly injecting the BSA/polymer dispersion into the PEG solution. The stirrer speed was then reduced and the mixture was left standing overnight.

The stirrer speed was set at 8 again and then 400 ml of deionized water were added to reduce the viscosity in order to enable filtration. The suspension was then filtered using a Millipore membrane filter, Type DV, pore size 0.65 $\mu$m, washed with water (3×300 ml) and dried in vacuum overnight.

The resulting microparticles were spherical with a particle diameter of 10–50 $\mu$m and contained 6.3% of BSA (w/w).

The resulting microparticles were then subjected to an in vitro release test in 30 mM sodium phosphate pH 7.4 at 37°

C., with intermittent agitation. The studies were conducted by suspending 40 mg of microspheres in 1.5 ml of buffer. At specified time points, 1 ml of the buffer was withdrawn and replaced with fresh-buffer. The results are shown in FIG. 1. Sustained release of BSA was achieved for 28 days as is shown in FIG. 1.

EXAMPLE 2

The same procedure was performed as in example 1 except that 2% (w/w) polyvinyl alcohol (PVA, mw=22000, Fluka)in water was used instead of the polyethylene glycol solution.

The resulting microspheres had a particle diameter of 1–2 mm and contained 7.0% of BSA. An in vitro release test was conducted as in example 1 and the results are shown in FIG. 1. Sustained release for about 2 days was achieved with this formulation. The large size would not have permitted injection using acceptable needles.

EXAMPLE 3

The same procedure was performed as in example 1 except that the an Ystral homogenizer was used instead of said stirrer when adding the BSA/polymer dispersion. After addition of the BSA/polymer dispersion the homogenizer was replaced by the 4-bladed propeller stirrer.

The resulting microspheres had a particle diameter of 1–5 $\mu$m and contained 5.5% of BSA. An in vitro release test was conducted as in example 1 and the results are shown in FIG. 1.

EXAMPLE 4

The same procedure was performed as in example 2 except that the an Ystral homogenizer was used instead of a stirrer when adding the BSA/polymer dispersion.

The resulting microspheres had a mean particle diameter of 10–40 $\mu$m and contained 5.8% of BSA. An in vitro release test was conducted as in example 1 and the results are shown in FIG. 1. Similar dissolution profiles were obtained for the preparations in examples 3 and 4 even though the size of the particle in example 3 was much smaller.

EXAMPLE 5

The same procedure was performed as in example 1 except that an ultrasonic bath (Transsonic 470/H, Elma) was used after the vortex mixing in order to obtain a finer water-in-oil emulsion. The BSA/polymer dispersion was sonicated for 1 minute.

The resulting microspheres had a mean particle diameter of 10–50 $\mu$m and contained 6.8% of BSA. An in vitro test was conducted as in example 1 and the results are shown in FIG. 1. Sustained release for 28 days was achieved. This shows that a more efficient emulsification of the inner aqueous phase results in a lower rapid initial release (burst) during the first days.

EXAMPLE 6
Preparation of BSA Loaded Microspheres

The following procedure was used to encapsulate Bovine Serum Albumin (BSA) in PLGA microspheres.

First a polymer solution was prepared by dissolving 0.126 g of polymer (Resomer 504 H, Boehringer Ingelheim) with 0.734 of ethyl acetate in a test tube. Then 15 mg of BSA (Sigma A-0281) were dissolved in 100 $\mu$l of 10 mM sodium phosphate pH 6.4.

The BSA solution was mixed with the polymer solution by vortex mixing (VF2, IKA-WERK) for one minute. The solution was withdrawn into a 2 ml syringe with a 21G needle. A 200 ml beaker-containing 50 ml of 40% (w/w) polyethylene glycol 20000 was fitted with a 4-bladed propeller stirrer. The BSA/polymer dispersion was slowly injected into the PEG solution during stirring at 240 rpm. The stirring speed was increased to 400 rpm for 10 seconds then the stirring speed was 60 rpm for one minute. The mixture was left standing unstirred for 4 hours. 200 ml of water were then added before filtration. The microsphere suspension was filtered using a Millipore membrane filter, Type DV, pore size 0.65 $\mu$m, washed with water and then freeze-dried overnight.

The resulting microparticles were spherical with a particle diameter of 10–50 $\mu$m and contained 9.7% of BSA (92% yield).

EXAMPLE 7
Preparation of Lactoglobulin Loaded Microspheres

The same procedure was performed as in example 6, except that 15 mg of Lactoglobulin (Sigma L-0130) in 100 $\mu$l 10 mM sodium phosphate pH 6.4 were used for encapsulation.

The resulting microparticles were spherical with a particle diameter of 10–100 $\mu$m and contained 9.9% of lactoglobulin (93% yield).

EXAMPLE 8

Preparation of Triptorelin Loaded Microspheres

The same procedure was performed as in example 6, except that 15 mg of Triptorelin pamoate (Bachem) were emulsified directly in the polymer solution by vortex mixing for one minute. The particle size of triptorelin particles was about 2–4 $\mu$m.

The resulting microparticles were spherical with a particle diameter of 20–100 $\mu$m and contained 6.3% of Triptorelin (59% yield).

EXAMPLE 9
Preparation of Desmopressin Loaded Microspheres

The same procedure was performed as in example 6, except that 15 mg Desmopressin acetate in 100 $\mu$l of 10 mM sodium phosphate pH 6.4 were used for encapsulation.

The resulting microparticles were spherical with a particle diameter of 10–50 $\mu$m and contained 8.3% of Desmopressin (78% yield).

EXAMPLE 10

Preparation of Insulin Loaded Microspheres

The same procedure was performed as in example 6, except that 15 mg Insulin (Sigma I-5500) were emulsified directly in the polymer solution by vortex mixing for one minute. The particle size of the insulin particles was about 5–10 $\mu$m.

The resulting microparticles were spherical with a particle diameter of 10–50 $\mu$m and contained 9.3% of Insulin (88% yield).

EXAMPLE 11
Preparation of DNA Loaded Microspheres

The same procedure was performed as in example 6, except that 100 $\mu$l of Herring Sperm DNA (Promega)(10 mg/ml) were used for encapsulation.

The resulting microparticles were spherical with a particle diameter of 10–50 $\mu$m and contained 0.07% of DNA (10% yield).

EXAMPLE 12

Preparation of Bovine Serum Albumin in 50% PEG 10k

The same procedure was performed as in example 6, except that 50% of PEG 10k was used as the external phase.

The resulting microparticles were spherical and contained 1.77% of BSA. This should be compared to 6.3% in example 1.

EXAMPLE 13

Preparation of Bovine Serum Albumin in 30% PEG 35k

The same procedure was performed as in example 1 except that 30% of PEG 35k was used as the external phase.

The resulting microparticles were spherical and contained 5.42% of BSA. This should be compared to a core load of 6.3% in example 1.

What is claimed is:

1. A method of encapsulating an active substance in a biodegradable polymer, which comprises:
   a. dissolving said biodegradable polymer in an organic solvent therefor;
   b. dispersing said active substance in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the absence of any surfactant, such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

2. A method of encapsulating an active substance in a biodegradable polymer, which comprises:
   a. dissolving said biodegradable polymer in an organic solvent therefor;
   b. dispersing said active substance, which has a particle size within the range of about 0.5–20 $\mu$m, in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the absence of any surfactant, such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

3. A method of encapsulating an active substance in a biodegradable polymer, which comprises:
   a. dissolving said biodegradable polymer in an organic solvent therefor;
   b. dispersing said active substance, which has a particle size within the range of about 0.5–10 $\mu$m, in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the absence of any surfactant, such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

4. A method of encapsulating an active substance in a biodegradable polymer, which comprises:
   a. dissolving said biodegradable polymer in an organic solvent therefor;
   b. dispersing said active substance, which has a particle size within the range of about 0.5–3 $\mu$m, in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the absence of any surfactant, such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

5. A method of encapsulating an active substance in a biodegradable polymer, which comprises:
   a. dissolving said biodegradable polymer in an organic solvent therefor;
   b. dispersing said active substance in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the presence of an aqueous polyethylene glycol solution having a polyethylene glycol concentration within the range of 30–55% (w/w), such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

6. A method of encapsulating an active substance in a biodegradable polymer, which comprises:
   a. adissolving said biodegradable polymer in an organic solvent therefor;
   b. dispersing said active substance in the organic solution obtained in step (a), to provide a dispersion with the active substance as the inner phase thereof; and
   c. subjecting the dispersion obtained in step (b) to an encapsulation operation with an aqueous polyethylene glycol solution as a continuous phase, performed in the presence of an aqueous polyethylene glycol solution having a polyethylene glycol concentration within the range of 30–50% (w/w), such that micro- or nanoparticles having the active substance encapsulated therein are obtained;
   wherein the biodegradable polymer is homo- or copolymers prepared from $\alpha$-hydroxy acids or cyclic dimers of $\alpha$-hydroxy acids or a combination thereof.

\* \* \* \* \*